(12) United States Patent
Lipshitz et al.

(10) Patent No.: US 6,902,577 B2
(45) Date of Patent: Jun. 7, 2005

(54) INTRAOCULAR LENS IMPLANT WITH MIRROR

(75) Inventors: Isaac Lipshitz, 89A Hanassi St., Herzlyia (IL); Haya Ruchvarger, Tel Aviv (IL)

(73) Assignee: Isaac Lipshitz, Hertzlia (IL)

( * ) Notice: Subject to any disclaimer, the term of this patent is extended or adjusted under 35 U.S.C. 154(b) by 283 days.

(21) Appl. No.: 10/108,458

(22) Filed: Mar. 29, 2002

(65) Prior Publication Data

US 2003/0187503 A1 Oct. 2, 2003

(51) Int. Cl.[7] .................................................. A61F 2/16
(52) U.S. Cl. ........................ 623/6.31; 623/6.32; 623/4.1
(58) Field of Search ............................... 623/6.11, 6.14, 623/6.19–6.21, 6.23–6.31, 6.51, 6.52, 6.56

(56) References Cited

U.S. PATENT DOCUMENTS

| | | | | |
|---|---|---|---|---|
| 4,759,761 | A | * | 7/1988 | Portnoy |
| 5,139,325 | A | * | 8/1992 | Oksman et al. |
| 5,166,711 | A | * | 11/1992 | Portney |

* cited by examiner

*Primary Examiner*—David H. Willse
*Assistant Examiner*—Hieu Phan
(74) *Attorney, Agent, or Firm*—Mark M. Friedman

(57) ABSTRACT

An intraocular implant for implantation into the interior of an eye is disclosed. The intraocular implant includes a body member, the body member has an anterior surface and a posterior surface, and has optical properties, and, at least one mirror, wherein the at least one mirror is contained within the body member.

48 Claims, 9 Drawing Sheets

INTRAOCULAR LENS IMPLANT WITH MIRROR

FIELD AND BACKGROUND OF THE INVENTION

The present invention relates to an intraocular insert for implantation in the interior of the human eye and, more particularly, to an intraocular implant with at least one mirror.

Macular degeneration is a disorder in which the central retinal area (the macula) degenerates, e.g., because of age (age-related macular degeneration, or AMD), diabetic retinopathy, ocular vascular accidents or diseases, retinal dystrophies (such as, for example, cone dystrophy), central nervous system (CNS) diseases, etc. These disorders in the macular area cause difficulty in central vision such that the afflicted person finds it difficult to read, drive, or perform other daily activities that require fine, sharp, central vision, but the individual's peripheral vision remains unaffected.

AMD is a common cause of visual loss among people over the age of 60. The risk of developing AMD is nearly 30% in those over age 75.

Low vision aids such as special telescopic or microscopic eyeglasses that create a magnification of the object on the retina have been used in the treatment of this condition. However, when an outside telescope is used, the visual field is very narrowly restricted, and therefore the afflicted person has to move his or her head back and forth to follow the lines being read. An alternative has been an intraocular implant containing a telescope (as described in Applicant's U.S. Pat. Nos. 5,354,335, 5,391,202, 5,814,103, 5,876,442, 5,928,283, 6,007,579 and 6,066,171). Laser photocoagulation and photodynamic therapy, as well as vitamin supplements, are also used in the treatment of this condition. Limitations to the use of the intraocular implants with a telescope include that these implants can not be used in both eyes—one eye is needed for improved central vision and one for peripheral vision. The IOL with the telescope (also known as an implantable miniaturized telescope, or IMT) decreases peripheral vision and interferes with the pupillary opening. The IOL with the telescope has a black posterior part that does not allow light to enter the eye, except through the telescope, as that would cause stray light and glare. The pupil has to be narrowed so that the pupil covers the black part of the IOL. With use of the IOL with the telescope there is a considerable reduction in the amount of light that enters the eye. It is reduced by up to 9-fold for a 3× magnification, (that is, only ⅑ of the light enters the eye), depending on the size of the opening of the telescope's cylinder. Further, there is a limit to the amount of magnification permitted by the geometry and the size of the telescope so that one can not achieve higher magnification without further restricting the visual field. Furthermore, use in only one eye causes anisoconia with a difference in image size between the eyes. In addition, laser or photodynamic therapy is difficult to perform through an IOL with a telescope.

In addition, it would be desirable to have an intraocular implant that could be adapted so as to be used for treatment of other diseases and problems of the eye. For example, such an intraocular implant could be used for treatment of diseases and processes that cause defects in peripheral vision, including inherited retinal disorders casusing retinitis pigmentosa, and glaucoma as examples. Further applications for such an intraocular implant include increased image magnification, increased illumination and the elimination of certain wavelengths of light, such as ultraviolet light. For example, an implant providing increased illumination and increased magnification would be desirable for use in the treatment of regular cataract patients.

There is thus a widely recognized need for, and it would be highly advantageous to have, an intraocular implant for treatment of defects in central vision, including AMD and other disorders of the macula, as well as for disorders of peripheral vision, and other disorders of vision, such as regular cataracts, devoid of the above limitations.

SUMMARY OF THE INVENTION

According to the present invention there is provided an intraocular implant for implantation in the interior of a human eye for treatment of defects in central vision, and of peripheral vision.

According to the present invention there is provided an intraocular implant for implantation into the interior of an eye, the eye having a pupil, an iris, and a retina, the retina having a macula, the implant including: a body member, the body member having an anterior surface and a posterior surface, and having optical properties, and, b. at least one mirror, wherein the at least one mirror is contained within the body member.

According to further features in preferred embodiments of the invention described below, the implant is adapted for a position of fixation into the eye, the position of fixation being selected from the group consisting of anterior chamber fixation, posterior chamber fixation, capsular bag fixation, scleral fixation, intra-vitreous fixation, sulcus fixation, and iris supported fixation.

According to still further features in the described preferred embodiments the anterior surface is of convex configuration.

According to still further features in the described preferred embodiments the posterior surface is of convex configuration.

According to still further features in the described preferred embodiments the posterior surface is of planar configuration.

According to still further features in the described preferred embodiments the body member is non-foldable.

According to still further features in the described preferred embodiments the body member is foldable.

According to still further features in the described preferred embodiments the implant further includes at least one loop for fixation in the eye.

According to still further features in the described preferred embodiments the at least mirror is configured so as to reflect a viewed image onto a preferred position of the retina of the eye.

According to still further features in the described preferred embodiments the at least one mirror is constructed from a plurality of component parts.

According to still further features in the described preferred embodiments the at least one mirror is adapted for multi-focal focusing.

According to still further features in the described preferred embodiments the at least one mirror is adapted for correction of higher order optical aberrations.

According to still further features in the described preferred embodiments the at least one mirror consists of two mirrors.

According to still further features in the described preferred embodiments the two mirrors are a central mirror and a peripheral mirror.

According to still further features in the described preferred embodiments the central mirror has a shape with at least one characteristic selected from the group consisting of convex, concave, rounded, pointed, aspheric, irregular, fixed shape, and adjustable shape.

According to still further features in the described preferred embodiments the peripheral mirror has a shape with at least one characteristic selected from the group consisting of a complete circumferential ring, a partial circumferential ring, convex, concave, aspheric, circular, elliptical, fixed shape, and adjustable shape.

According to still further features in the described preferred embodiments the peripheral mirror is at least partially hidden beneath the iris of the eye.

According to still further features in the described preferred embodiments the central mirror has an aperture therethrough.

According to still further features in the described preferred embodiments the implant further includes at least one adjustment mechanism for adjusting at least one feature of the at least one mirror.

According to still further features in the described preferred embodiments the adjustment mechanism is selected from the group consisting of a micromechanical mechanism, an electromagnetic mechanism, a photoelectric mechanism, and a piezoelectric mechanism.

According to still further features in the described preferred embodiments the at least one feature is selected from the group consisting of shape of the at least one mirror, curvature of the at least one mirror, and position of the at least one mirror.

According to still further features in the described preferred embodiments the implant is adapted for the treatment of presbyopia by the adjustment of the feature of the at least one mirror.

According to still further features in the described preferred embodiments the at least one adjustment mechanism is operable from outside the eye.

According to still further features in the described preferred embodiments the at least one adjustment mechanism is operable from outside the eye by an adjustment control element selected from the group consisting of a laser, ultrasound, light, a frequency emitter, an electromagnetic force element, a temperature control element, and a pressure control element.

According to still further features in the described preferred embodiments the implant further includes at least one prism.

According to still further features in the described preferred embodiments the at least one prism is adapted so as to divert at least a portion of a viewed image to a preferred part of the retina of the eye.

According to still further features in the described preferred embodiments the at least one prism is adapted so as to produce a continuity on the retina of the eye of a reflected visual image with a transmitted, unreflected image.

According to still further features in the described preferred embodiments the at least one prism is selected from the group consisting of a holographic lens and a fresnel.

According to still further features in the described preferred embodiments the at least one mirror is coated with a reflectance altering material for altering at least one light reflectance property of the at least one mirror.

According to still further features in the described preferred embodiments the reflectance altering material is adapted for altering transmission of light through the implant.

According to still further features in the described preferred embodiments the reflectance altering material is adapted for blocking at least one specified spectrum of wavelength of light transmission through the implant.

According to still further features in the described preferred embodiments the implant further includes at least one filter for adjusting the light transmission through the implant.

According to still further features in the described preferred embodiments the implant further includes at least one lens.

According to still further features in the described preferred embodiments the implant further includes a conformer, the conformer adapted for implantation into a structure of the eye, the conformer and the body member being adapted such that the body member is capable of being inserted and fixed into the conformer.

According to still further features in the described preferred embodiments the conformer further includes at least one optical component.

According to still further features in the described preferred embodiments the conformer has at least one optical property.

According to still further features in the described preferred embodiments the conformer is non-foldable.

According to still further features in the described preferred embodiments the conformer is foldable.

According to still further features in the described preferred embodiments the conformer further includes at least one loop for fixation in the eye.

According to still further features in the described preferred embodiments the implant is adapted so that the body member may be changed within the conformer.

According to still further features in the described preferred embodiments the body member is solid.

According to still further features in the described preferred embodiments the body member encloses an inner cavity.

According to still further features in the described preferred embodiments the cavity is filled with a material with desired optical properties.

According to still further features in the described preferred embodiments the material is selected from the group consisting of a gas, air, a liquid, water, an oil, a solid, and a material with a graded index of refraction.

According to still further features in the described preferred embodiments the at least one mirror is adapted for transmission of a laser beam for medical purposes.

According to still further features in the described preferred embodiments the implant is adapted for inverting an image.

According to still further features in the described preferred embodiments the implant is adapted for magnifying an image According to still further features in the described preferred embodiments the implant is adapted for minifying an image.

According to still further features in the described preferred embodiments the implant is adapted for moving an image to a particular position on the retina.

According to still further features in the described preferred embodiments the implant is adapted for changing a visual field.

According to still further features in the described preferred embodiments the implant is adapted for increasing peripheral vision.

According to still further features in the described preferred embodiments the implant is adapted for improving central vision.

According to still further features in the described preferred embodiments the implant is adapted for altering an intensity of light entering the eye.

According to still further features in the described preferred embodiments the implant is adapted for altering at least one spectrum of wavelength of light entering the eye.

According to still further features in the described preferred embodiments the implant is adapted for treatment of a disorder of central vision.

According to still further features in the described preferred embodiments the disorder of central vision is age-related macular degeneration.

According to still further features in the described preferred embodiments the implant is adapted for treatment of a disorder of peripheral vision.

According to still further features in the described preferred embodiments the disorder of central vision is a tapetoretinal degeneration.

According to still further features in the described preferred embodiments the implant is adapted for treatment of a cataract.

The present invention successfully addresses the shortcomings of the presently known configurations by providing an intraocular implant containing at least one mirror, which can be used in the treatment of any ocular problem, including disorders of central and peripheral vision. Whereas the IOL with a telescope is intended not to allow peripheral light to enter the eye as it causes visual disturbances, thus narrowing the pupillary opening, in the present invention the pupil is not affected and the pupil functions normally.

In the IOL with a telescope there is a considerable reduction of the amount of light that enters the eye. In the IOL with a telescope, the amount of light entering the eye is reduced by up to 9 fold (only ⅑ of the light enters the eye), depending on the size of the opening of the telescope's cylinder, while all the other light is blocked. In the present invention there is no decrease of the amount of light that enters the eye, as the pupil is not affected. On the contrary the amount of light that enters the eye can be increased by using special coatings on the mirrors that collect more light and give better contrast.

Another advantage, among many others, of the present invention is the easing of restrictions of patient selection criteria for implantation, as use of the device is no longer restricted to patients that have similar visual acuities in both eyes, and visual acuity lower than a certain standard in both eyes. The present invention can be implanted in a patient that has central visual problems in both eyes without taking into account the relative visual acuity of the other eye. Further it can be used for both dry-type as well as wet-type macular degeneration. In addition, contrary to the IOL with a telescope, it can be used for other purposes including for treatment of defects in peripheral vision, for image magnification, including, for example, after regular cataract surgery, and for eliminating specific wavelengths of light such as ultraviolet light, for example.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
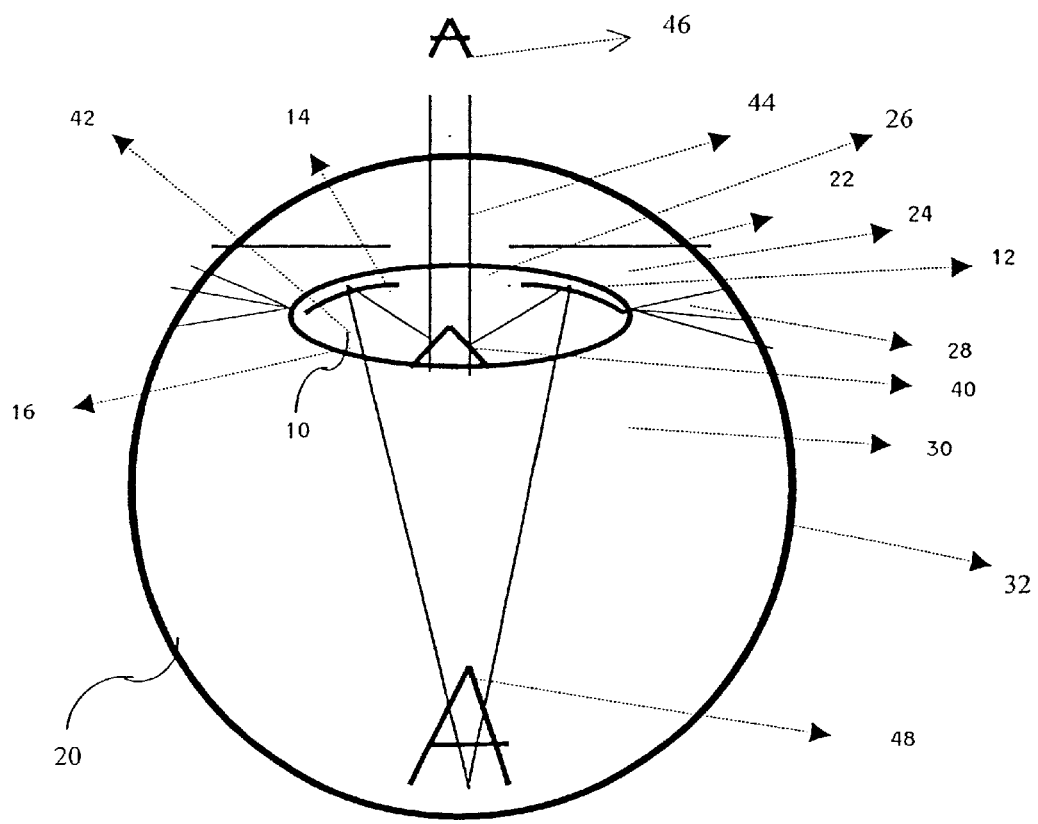
FIG. 1 illustrates a horizontal section of an eye with a preferred embodiment of the intraocular insert of the present invention in place.

The present invention is of an intraocular insert for implantation in the interior of the human eye and, more particularly, to an intracular implant containing at least one mirror, which can be used in the treatment of regular cataracts, and of disorders of central, as well as of disorders of peripheral, vision. Specifically, the present invention can be used to treat AMD and other macular degenerations. Modifications of the intraocular insert can be used for the treatment of other ocular disorders including retinitis pigmentosa and glaucoma and other causes of impaired peripheral vision, for example.

The principles and operation of an intracular implant containing at least one mirror according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates a horizontal section of a human eye (20), illustrating the cornea 22, the iris 24, the pupil 26, the zonula 28, the vitreous 30 and the retina 32. FIG. 1 further illustrates a preferred embodiment of an intraocular implant, generally designated 10, constructed in accordance with the present invention, and implanted in eye 20. The means for fixing implant 10 in eye 20 are not described herein, as many such means are known for mounting artificial intraocular implants and lenses and can be used for fixing intraocular implant 10 in place. In various configurations of the present invention, implant 10 is implanted so as to replace the normal lens of eye 20, while in other configurations implant 10 is used in conjunction with the normal lens of eye 20. In various alternate configurations, implant 10 can be implanted in various compartments and by various techniques including fixation in the anterior or posterior chamber, capsular bag, by sulcus fixation, scleral fixation, intravitreous fixation or iris supported as non-limiting examples.

Figure 9:
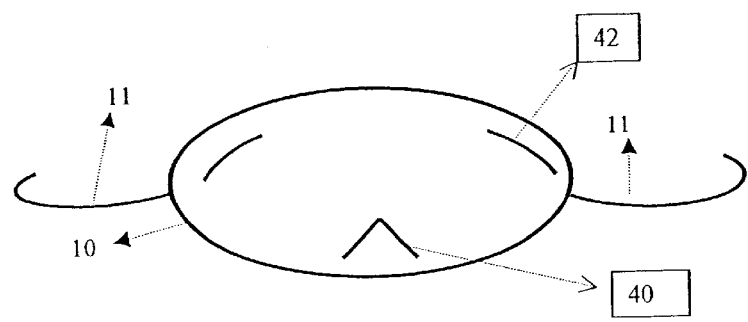
Figure 9:
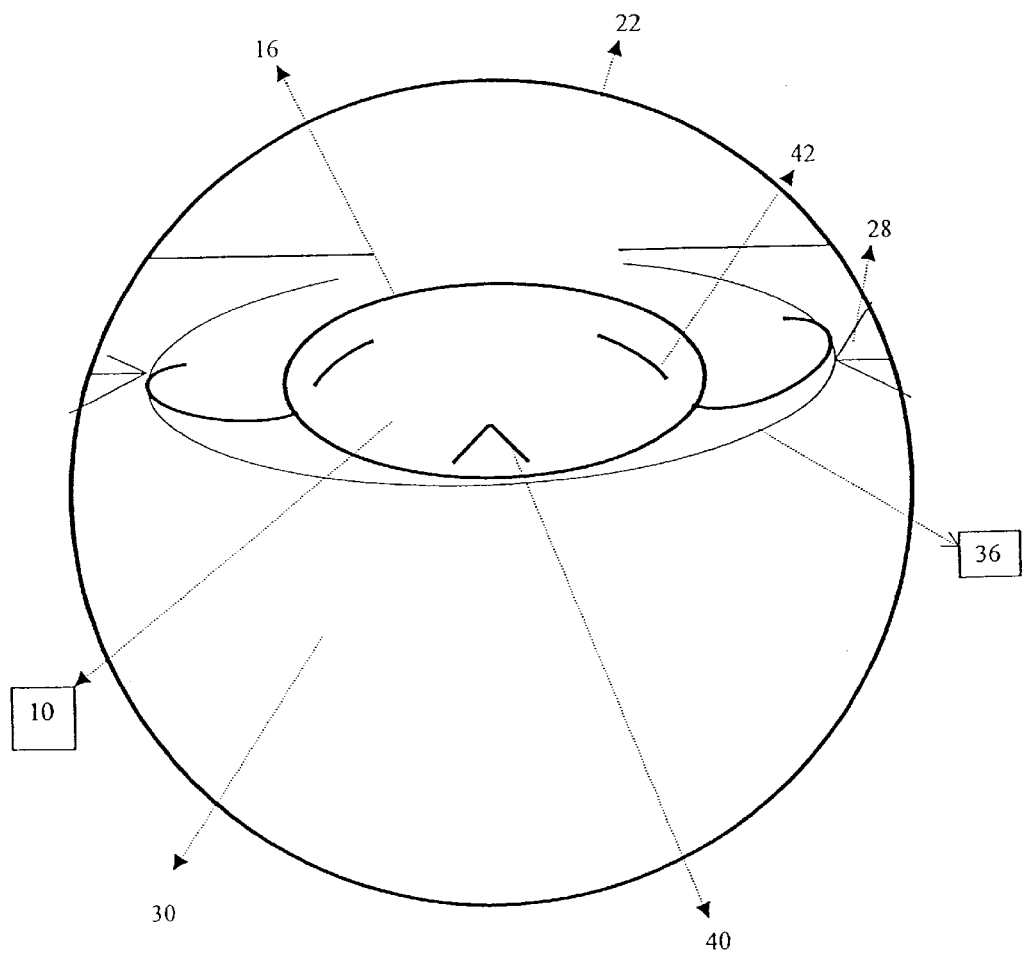

The intraocular implant 10 includes a body member 12, of generally convexo-convex or convexo-plano configuration; that is, its front or anterior face 14 facing the anterior side of eye 20 is of convex configuration, and similarly its rear or posterior face 16 facing the posterior side of eye 20 is of convex (or planar) configuration; or may be of any other configuration. The dioptic and other optical properties of body member 12 are one parameter determining the visual correction of implant 10. Both surfaces may be of any dioptic power and may include additional optical properties such as a prism, fresnel, index graded optics or aspheric, as non-limiting examples. Body member 12 is generally fabricated from the same material as conventionally used for making intraocular lenses, such as a transparent plastic (e.g., polymethylmethacrylate, acrylic, or silicone), glass, sapphire or any other material suitable for use in the construction of intraocular implants. In various preferred embodiments, body member 12 may be made of a rigid material (and be a hard lens) or may be foldable (and be a soft lens). Use of a material such as an acrylic or silicone that allows body member 12 to be soft and foldable allows the insertion of implant 10 through a smaller surgical incision. As illustrated in FIG. 9, implant 10 may also include at least one loop 11 for holding and fixing implant 10 inside the capsular bag 36 of eye 20. Implant 10 fills the entire lenticular capsular bag 36 in certain configurations and applications, and in other configurations and applications does not fill the entire lenticular capsular bag 36. Particularly when implant 10 does not fill the entire capsular bag, various configurations of the at least one loop 11 fixes implant 10 within the capsular bag. In configurations where only one loop 11 is employed, loop 11 is preferably configured as a ring.

Figure 2:
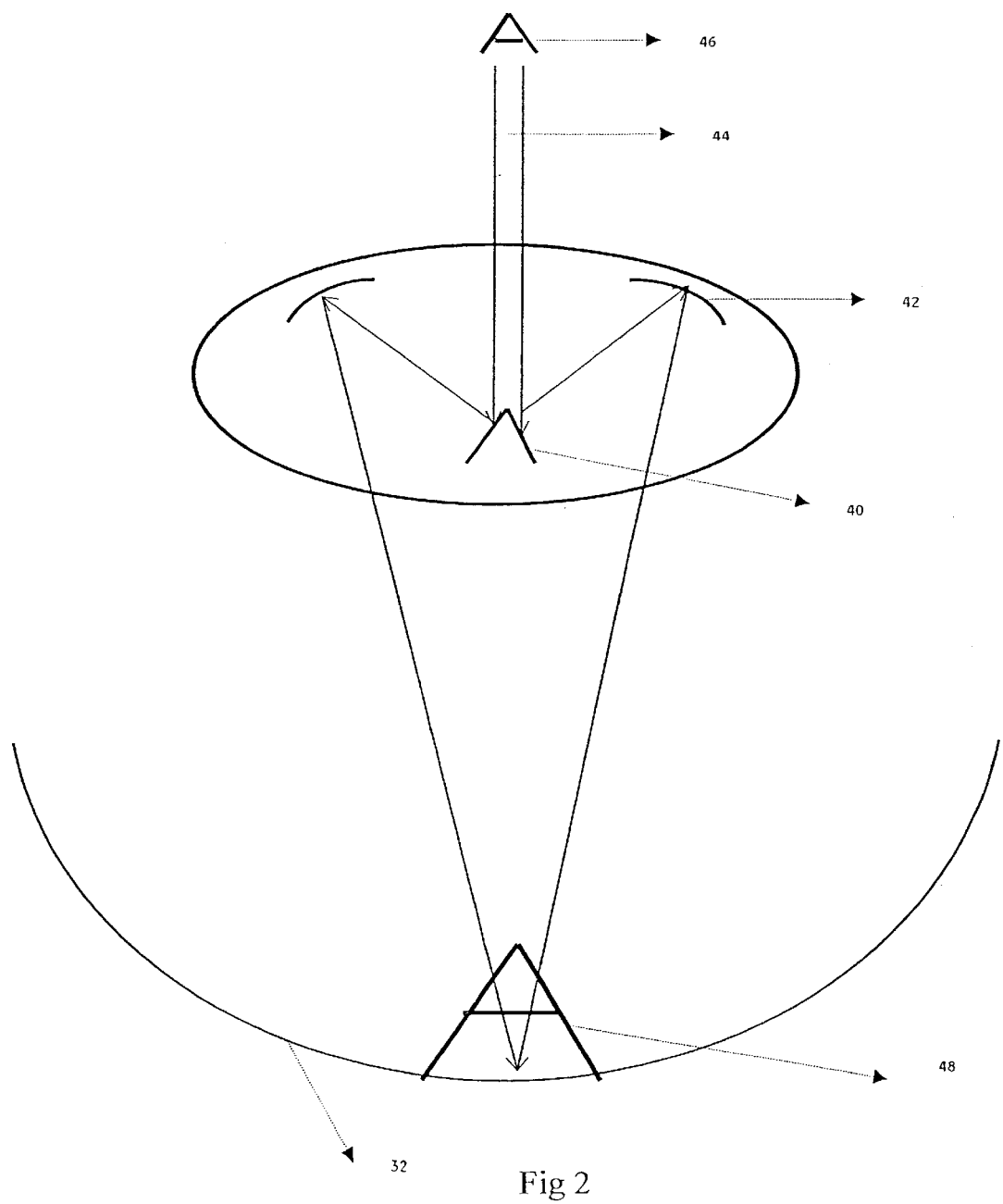
FIG. 2 is a schematic diagram illustrating the principles of a preferred embodiment of the present invention.

Incorporated into body member 12 of implant 10 is at least one mirror. Two are illustrated in FIG. 1 and are designated 40 and 42. The principle and object of implant 10 containing the at least one mirror is to improve vision, by changing the image on the retina. For example, implant 10 can be used to enlarge the optical image on the retina of eye 20 in an individual affected with an ocular disorder such as AMD and can be used to reflect the image to a desired position on retina 32. As illustrated in FIG. 2, the at least one mirror, here illustrated in a non-limiting exemplary illustration with two mirrors, 40 and 42, function to gather light rays 44 of object 46 with a first, central mirror 40, and reflect the light to second (peripheral) mirror 42 before directing the light and focusing the image 48 on the retina 32. The arrangement of mirrors can be used to move, by use of mirrors or additionally prisms (as discussed hereinunder), the image to a preferred position on retina 32 where sight is, for example, better preserved than at the diseased portion of the macula. The arrangement of mirrors typically gives a wider aperture of vision than a refracting telescopic system using lenses and avoids chromatic and other optical aberration.

Thus there are essentially two parameters of implant 10 that determine the visual correction produced by implant 10. The dioptic and other optical properties of body member 12 are one parameter determining the visual correction of implant 10. The second parameter is based on the properties of the at least one mirror. As a non-limiting example, in particular preferred embodiment, the properties of body member 12 determine the correction of peripheral vision and the magnification accomplished by the arrangement of the at least one mirror determines central vision. Normal light is transmitted directly and normally through body member 12 while central light is diverted to the at least one mirror.

Figure 3:
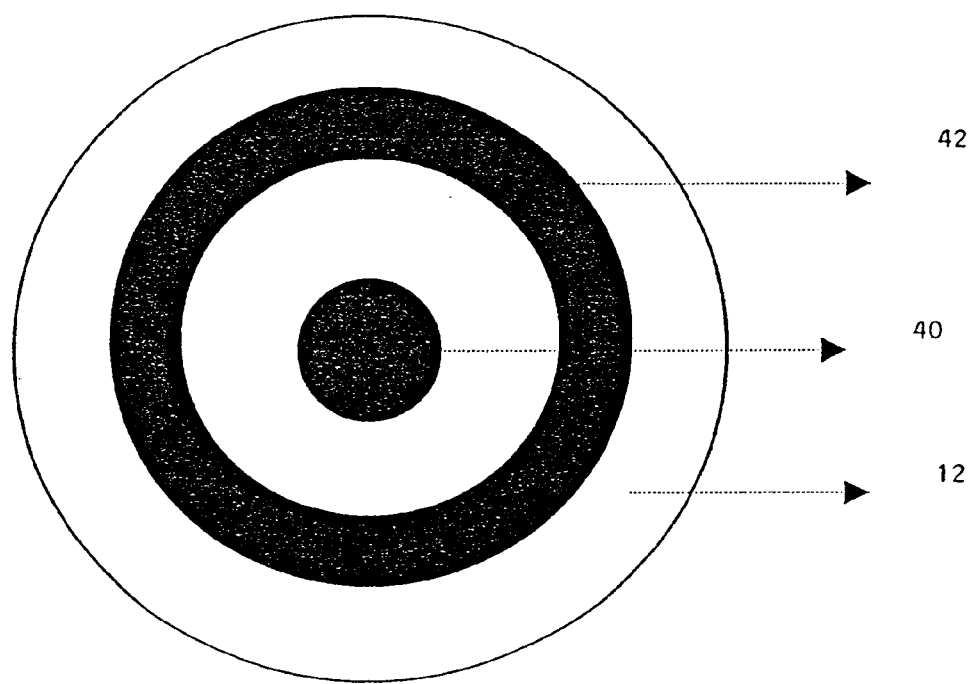
FIG. 3 is a frontal view of a preferred embodiment of the intraocular insert according to the present invention.

In various configurations, central mirror 40 may be convex or concave, and rounded or pointed and therefore take various shapes including, but not limited to shapes such as: U or ∩, V or ∧, as well as any other aspheric or irregularly shaped surface. Second mirror 42 is a circumferential ring (complete or partial, generally circular or elliptical, for example) hidden (completely or partially) beneath iris 24 as is illustrated in FIGS. 1 and 3. Alternatively an artificial pupillary aperture can be created by the mirror. Like reference numerals refer to like parts throughout the figures of the drawing. In such a position mirror 42 does not affect the passage of light rays into eye 20 as mirror 42 is under the iris 24 which already blocks the entry of light. Pupil 26 is not affected and functions normally. Thus the position of mirror 42 and, in some configurations, a gap in mirror 42, defines the size of pupil 26. Mirror 42 may take different shapes in various preferred embodiments, convex or concave or aspheric, as non-limiting examples, and may be of a fixed shape and (angle or degree of) curvature or may be adjustable as described hereinunder. In certain preferred embodiments (for example, where implant 10 is placed in the vitreous) only a single mirror is used. In others, more than two mirrors may be used, for example, to invert the image, or to increase the degree of magnification. In other configurations, for example, the at least one mirror can be used to make the image on the retina smaller, for example for the treatment of an anisometropia, or a wide angle mirror, like that used for rear or side view mirrors in an automobile can be employed to increase peripheral vision. Other purposes for different selections of different configurations of the at least one mirror include, for example, to improve the amount of light entering the eye or to eliminate certain wavelengths of light while permitting others. Further, the at least one mirror can be adapted for multi-focal focusing.

Central mirror 40, which is preferably about 0.1 to 4.5 mm, and more preferably 0.2 to 3.5 mm in size, and most preferably about 1 to 2 mm in size, is placed in front of the macula of retina 32. Though mirror 40 may provide a small obstruction blocking light rays from directly impacting on the macula of retina 32, the macula is the portion of retina 32 that is damaged by the extant disease process in any case. In some embodiments central mirror 40 has an aperture (which may be centrally placed, as a non-limiting example) to allow direct and reflected light rays to pass therethrough and impact on retina 32. In such cases mirror 40 has a configuration that appears like ∧ rather than ∧ for example. Thus the at least one mirror may be constructed from more than one component part or piece. For example, the peripheral mirror 42 too may be constructed from separate pieces and not necessarily be continuous.

One of ordinary skills in the art would know how to operatively assemble the components of implant 10. Additional components may be required to connect and fix into place the various individual elements of implant 10.

In certain configurations, the at least one mirror is custom designed of a shape determined by the wavefront of a specific eye and adapted so as to correct for higher order optical aberrations.

The size of the entire implant 10 is preferably about 4–10 mm, (and most preferably 6–10 mm) by about 1–6 mm (and most preferably 4–5 mm), apart from any attached loops for fixation. The width of implant 10 is preferably less than the 5 mm size of the capsular bag, when implanted therein. When fixed in the vitreous, there is more space, and implant 10 may be of a larger size. Second mirror 42 is preferably about 0.2 to 5 mm in longest diameter.

Figure 4:
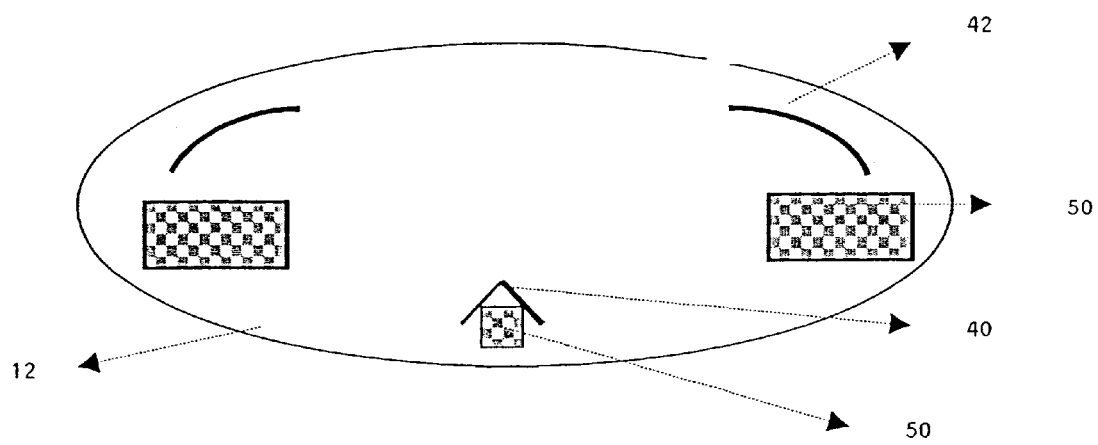
FIG. 4 is a horizontal section of an alternate preferred embodiment of the intraocular insert according to the present invention.

FIG. 4 illustrates a further preferred embodiment of the present invention in which the shape or curvature of the at least one mirror, for example, mirror 40 or mirror 42, is adjustable. Operationally connected to the at least one mirror (in various alternate configurations, either mirror 40 and/or mirror 42) is at least one adjustment mechanism 50. Adjustment mechanism 50 is operational from outside of or inside eye 20 to change the curvature of mirror 40 and/or 42 so as to change the magnification of image 48. Further adjustment mechanism 50 in certain configurations is adapted to move the position of the at least one mirror, for example in an anterior/posterior direction or to the sides. Such movement in position of the at least one mirror 40 or 42 is particularly useful in the treatment of presbyopia. Adjustment mechanism 50 in certain embodiments contains, as a non-limiting example, a micromechanical element that exerts tractional forces on mirror 40 and/or 42 so as to change the curvature of mirror 40 and/or 42. Adjustment mechanism in other embodiments may also be an electromagnetic, a photoelectric or piezoelectric element as further non-limiting examples. Adjustment mechanism 50 may include a power source (not illustrated individually) in certain configurations, which may be, as a non-limiting example, a photoelectric cell. Such a power source in certain configurations is further used to move the position of implant 10 anteriorly and posteriorly, for example, or to constrict the pupil of the eye. Adjustment mechanism 50 is operable from outside eye 20 for example by a laser, light, ultrasound or other frequency emission, or an electromagnetic force, or for example, by a change in temperature, either heat or cold, or pressure. The degree of magnification of the implant is affected by the number, shape, curvature and configurations of mirrors, the composition, shape and curvature of the body member, and any other optical elements placed in front of the eye such as lenses or spectacles.

Figure 5:
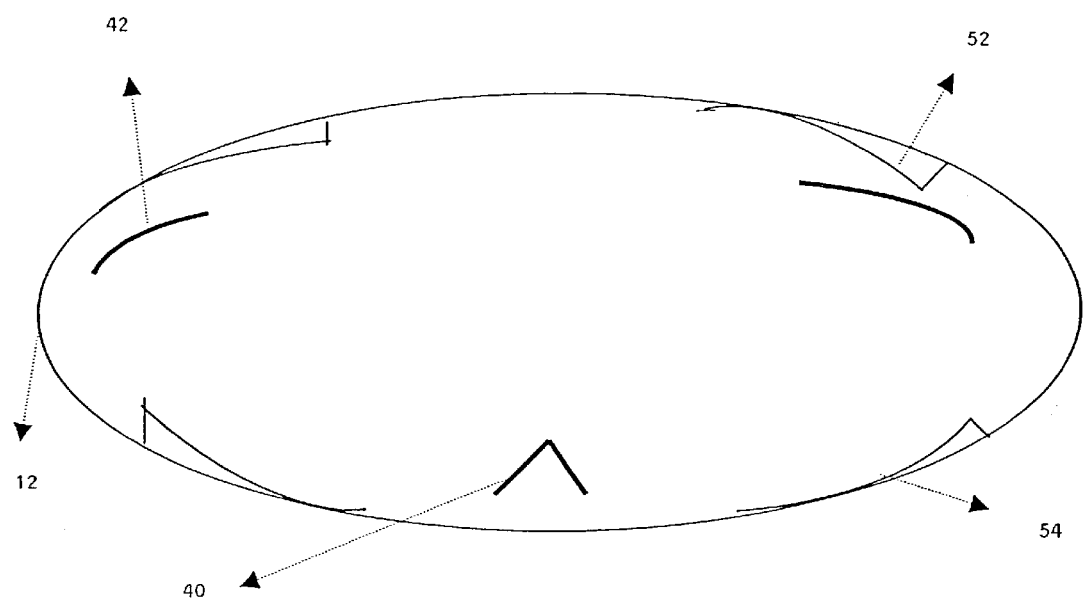
FIG. 5 is a horizontal section of a further alternate preferred embodiment of the intraocular insert according to the present invention.

FIG. 5 illustrates another preferred embodiment in which the intraocular implant 10 further includes at least one prism 52. Prism 52 is used for example to divert all or portions of the vision, for example both central image 48 as well as the peripheral vision to other parts of the macula or of retina 32. At least one prism 52 can be placed in varying positions within implant 10 as illustrated in FIG. 5 by the illustrated second prism 54. The at least one prism (eg. 52) can be used to avoid an improper overlap of the reflected image 48 with other images on retina 32. The at least one prism (eg 52) can be used to displace a peripheral image and make it in continuity with the magnified central image 48. The image from the central vision is now magnified. In order to smooth the picture seen and prevent overlap of a large central image on the smaller adjacent image, the at least one prism 52 pushes aside the peripheral image to make room for the large central image and to allow for a single continuos smooth full picture. In various alternate preferred embodiments and configurations, the at least one prism 52 may be a separate element inside implant 10 (in those configurations wherein implant 10 is hollow) or the at least one prism 52 may be a holographic lens, a fresnel, or be produced by a difference of index of refraction of the various materials of implant 10. Thus the at least one prism 52 may be inside or outside body member 12.

Further, in certain configurations, the at least one mirror is coated with a material that alters the light reflectance properties of the at least one mirror. Such coating can be used for example, to collect more light and intensify the light transmission and the contrast of the reflected image as is desirable in patients with AMD. Further, alternate coatings can be used to block a certain spectrum of light (e.g., ultraviolet) so as to sharpen the image and also to reduce damage to retina 32. Further, in place of, or in addition to, the at least one prism 52, as illustrated in FIG. 5, implant 10 in certain preferred embodiments, contains at least one filter to change the spectrum of light impacting on retina 32. Such a change in spectrum can include both enhancements or reductions in the intensity or portion of the spectrum impacting on retina 32. In other preferred embodiments, at least one other optical component, for example at least one lens, may also be included in implant 10.

In alternate configurations, the precise arrangements of the at least one mirror (including the numbers, shapes, curvature, placement, and coating, for example, of the mirrors, as well as the presence of prisms or filters) can be used to determine the precise changes of the images reflected onto retina 32. Depending on the values for these parameters, implant 10 can be used to, as non-limiting examples, magnify, minify, move, or invert an image, increase or decrease the visual field, or introduce a prismatic inversion or change the intensity and/or spectrum of light entering the eye.

Defects in peripheral vision occur in other disorders of the eye, such as (inherited) tapetoretinal degeneratuions causing retinitis pigmentosa, and glaucoma for example. Peripheral vision involves the ability to perceive objects, gross movement, or sharp contrasts toward the sides and edges of the visual field. Use of a configuration of implant 10 in which the at least one mirror increases the visual field, for example through use of a wide angle mirror such as is conventionally employed in rear view car mirrors, can be used to treat such disorders which otherwise reduce peripheral vision.

Figure 6:
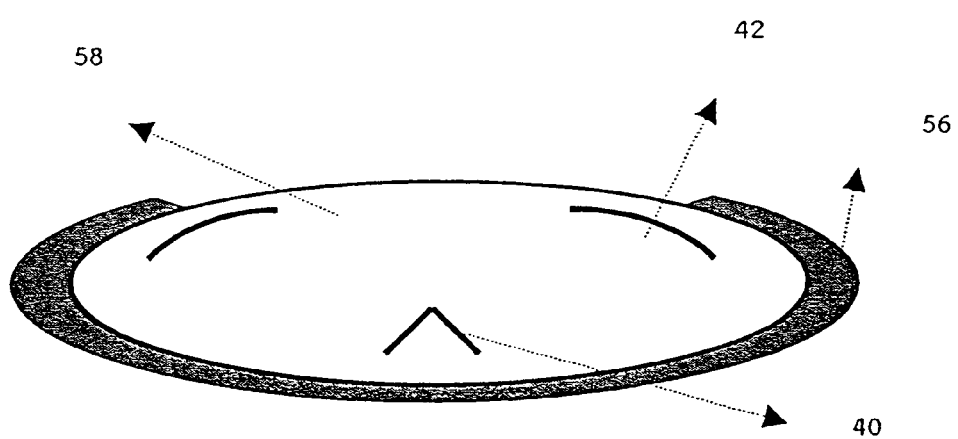
FIG. 6 is a horizontal section of a further alternate preferred embodiment of the intraocular insert according to the present invention.

FIG. 6 illustrates an alternate preferred embodiment of the implant 10 according to the present invention in which a carrier or conformer 56 is first inserted into a structure of the eye 20 (for example, to replace the patient's lens) and then body member 12 is inserted into conformer 56 as an inner insert 58. In this manner, inner insert 58 including body member 12 containing the at least one mirror can be more easily changed so as to change the treatment as the underlying disease changes and progresses. Further inner insert 58 can be rotatable from outside eye 20 or the position of inner insert 58 inside the eye can be changed in any other manner from outside the eye. Conformer 56 may, in certain configurations, also contain various optical components such as at least one lens or mirror or conformer 56 itself may have various optical properties. As is described hereinabove for body member 12 conformer 56 may be constructed from a hard (non-foldable) or soft (foldable) material. Conformer 56 placed in any structure of the eye, generally preferably into the lenticular capsule as a non-limiting example, and, in certain configurations, has at least one loop (not illustrated), analogous to the at least one loop 11 illustrated in FIG. 9 for fixation to an eye structure.

Figure 7:
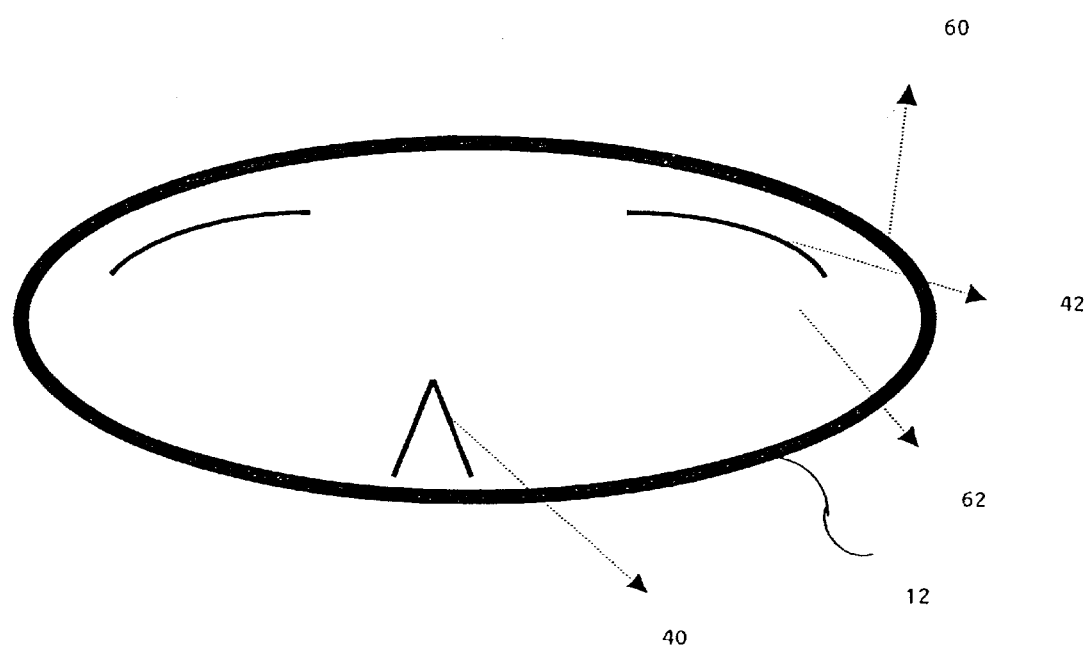
FIG. 7 is a horizontal section of a further alternate preferred embodiment of the intraocular insert according to the present invention.

FIG. 7 illustrates an alternate embodiment of implant 10 in which body member 12 is hollow rather than solid. In the embodiment illustrated in FIG. 7, body member 12 consists of an outer casing 60, fabricated from glass or any other biocompatible and suitable material, enclosing an inner cavity 62. The at least one mirror (two are illustrated in FIG. 7 and are designated 40 and 42) are placed and fixed (as necessary with fixation elements) within cavity 62. Cavity 62 may be filled with any suitable material depending on the index of refraction desired, including for example, air or other gases, water, oil, or other transparent liquids, another solid component, or a graded index of refraction material. The material in cavity 62 is also chosen based on the chemical properties of the material. For example, such a material is preferably inert, biocompatible, non-toxic, and suitable for the particular structure and configuration of implant 10.

Figure 8:
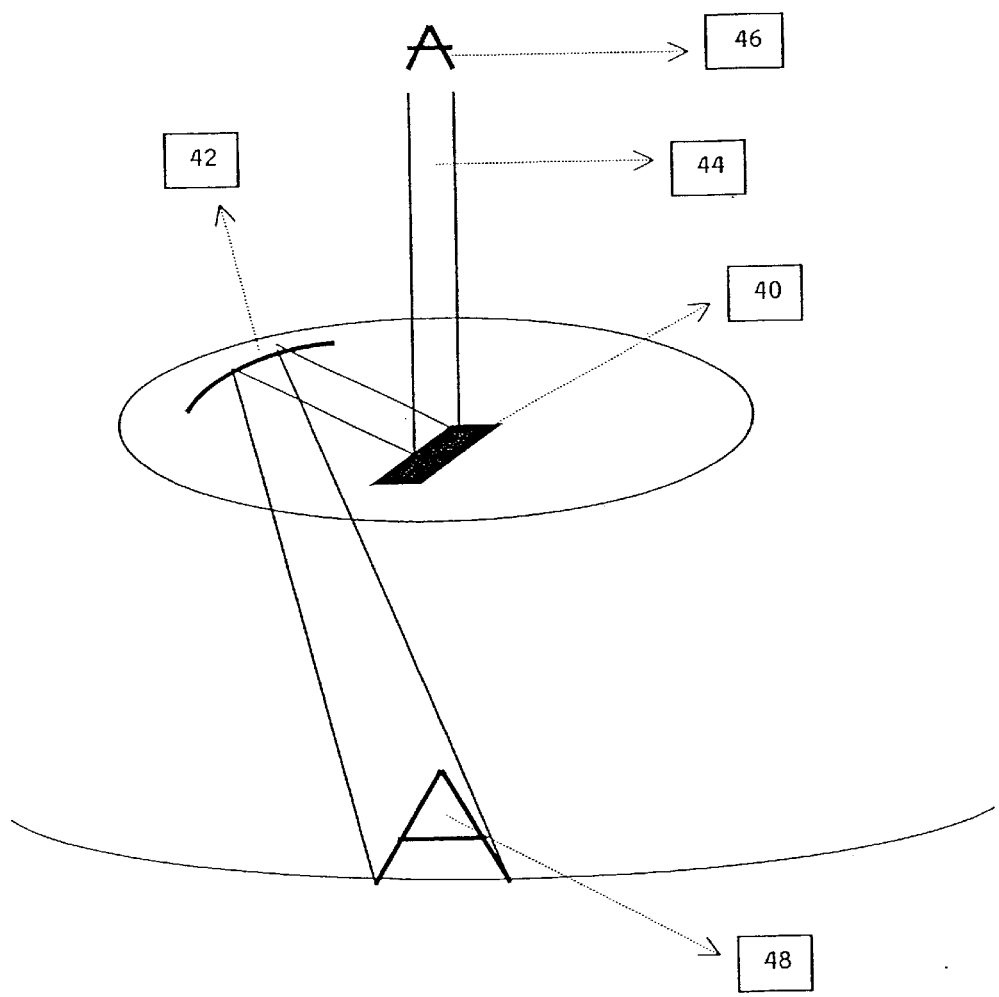
FIG. 8 is a horizontal section of another alternate preferred embodiment of the intraocular insert according to the present invention; and, FIG. 9 is a horizontal section of a further alternate preferred embodiment of the intraocular insert according to the present invention.

FIG. 8 shows an alternate configuration of implant 10. Such a configuration finds particular use, as a non-limiting example, in the treatment of a regular cataract. In the configuration illustrated in FIG. 8, two mirrors, 40 and 42, are illustrated. Mirror 40 for example has a planar configuration and mirror 42 is not fully circumferential.

Implant 10 according to the present invention can be used in both eyes. As opposed to the intraocular implant with a telescope there is no interference with the pupil size, peripheral vision or isoconia. In contrast to the intraocular implant with a telescope where there is a correlation between the magnification ability and the maximal image size, which confers a limitation, with implant 10 of the present invention, the magnification can be increased and the image size can be increased in an unlimited fashion. Further, treatment with laser or photodynamic therapy can be performed through implant 10, with the laser, for example, passing directly through implant 10 or reflecting off the at least one mirror. The at least one mirror in some configurations is adapted for transmission of a laser beam for medical purposes. The laser beam may be, for example, PDT, an argon laser, a krypton laser or a YAG laser or any other such laser as is used medically.

In various alternate configurations, implant 10 may find application for uses other than for treating disorders of central vision such as AMD, or those of peripheral vision, such as retinitis pigmentosa. For example, implant 10 may be adapted use to treat a patient suffering from a regular cataract or for after cataract surgery. Implant 10 may be used in "normal" eyes to magnify images, to increase the amount of light entering, or to change the spectrum of wavelengths of light permitted to enter the eye.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An intraocular implant for implantation into the interior of an eye, the eye having a pupil, an iris, and a retina, the retina having a macula, the implant comprising:
    a. a body member, said body member having an anterior surface and a posterior surface, said body member having optical properties, said body member being foldable; and
    b. at least one mirror, wherein said at least one mirror is contained within said body member.

2. The implant of claim 1, wherein said implant is adapted for a position of fixation into the eye, said position of fixation being selected from the group consisting of anterior chamber fixation, posterior chamber fixation, capsular bag fixation, scleral fixation, intra-vitreous fixation, sulcus fixation, and iris supported fixation.

3. The implant of claim 1, wherein said anterior surface is of convex configuration and wherein said posterior surface is one of a convex configuration and a planar configuration.

4. The implant of claim 1, wherein said at least mirror is configured so as to reflect a viewed image onto a preferred position of the retina of the eye.

5. The implant of claim 1, wherein said at least one mirror is constructed from a plurality of component parts.

6. The implant of claim 1, wherein said at least one mirror is adapted for al least one of multi-focal focusing and correction of higher order optical aberrations.

7. The implant of claim 1, wherein said at least one mirror consists of two mirrors, said two mirrors being a central mirror and a peripheral mirror.

8. The implant of claim 7, wherein said peripheral mirror is at least partially hidden beneath the iris of the eye.

9. The implant of claim 7, wherein said central mirror has an aperture therethrough.

10. The implant of claim 1, wherein said at least one mirror is coated with a reflectance altering material for altering at least one light reflectance property of said at least one mirror, said reflectance altering material being adapted for at least one function selected from the group consisting of: for altering transmission of light through the implant and for blocking at least one specified spectrum of wavelength of light transmission through the implant.

11. The implant of claim 1, wherein said body member encloses an inner cavity, wherein said cavity being filled with a material with desired optical properties, said material being selected from the group consisting of a gas, air, a liquid, water, an oil and a material with a graded index of refraction.

12. The implant of claim 1, wherein said at least one mirror is adapted for at least one function selected from the group consisting of: transmission of a laser beam for medical purposes, inverting an image, magnifying an image, magnifying an image, moving an image to a particular position on the retina, changing a visual field, increasing peripheral vision, improving central vision, altering an intensity of light entering the eye, altering at least one spectrum of wavelength of light entering the eye, for treatment of a disorder of central vision, treatment of age-relate macular degeneration, treatment of a disorder of peripheral vision, treatment of a tapetoretinal degeneration, and treatment of a cataract.

13. An intraocular implant for implantation into the interior of an eye, the eye having a pupil, an iris, and a retina, the retina having a macula, the implant comprising:
    a. a body member, said body member having an anterior surface and a posterior surface, said body member having optical properties, and, b. at least one mirror, wherein said at least one mirror is contained within said body member, wherein said body member and said at least one mirror are configured, such that a part of the light entering the eye arrives at the retina unreflected, thereby preserving at least part of the peripheral visual field.

14. The implant of claim 13, wherein said implant is adapted for a position of fixation into the eye, said position of fixation being selected from the group consisting of anterior chamber fixation, posterior chamber fixation, capsular bag fixation, scleral fixation, intra-vitreous fixation, sulcus fixation, and iris supported fixation.

15. The implant of claim 13, wherein said body member is non-foldable.

16. The implant of claim 13, wherein said body member is foldable.

17. The implant of claim 13, wherein said implant further includes at least one loop for fixation in the eye.

18. The implant of claim 13, wherein said at least one mirror is configured so as to reflect a viewed image onto a preferred position of the retina of the eye.

19. The implant of claim 13, wherein said at least one mirror is constructed from a plurality of component pads.

20. The implant of claim 13, wherein said at least one mirror is adapted for a function selected from the group consisting of multi-focal focusing and correction of higher order optical aberrations.

21. The implant of claim 13, wherein said at least one mirror consists of two mirrors.

22. The implant of claim 21, wherein said two mirrors are a central minor and a peripheral mirror.

23. The implant of claim 22, wherein said peripheral mirror is at least partially hidden beneath the iris of the eye.

24. The implant of claim 22, wherein said central mirror has an aperture therethrough.

25. The implant of claim 13, wherein said at least one mirror is coated with a reflectance altering material for altering at least one light reflectance property of said at least one mirror.

26. The implant of claim 25, wherein said reflectance altering material is adapted for at least one function selected from the group consisting of: for altering transmission of light through the implant, and for blocking at least one specified spectrum of wavelength of light transmission through the implant.

27. The implant of claim 13, wherein said at least one mirror is adapted for at least one function selected from the group consisting of: for transmission of a laser beam for medical purposes, for inverting an image, for magnifying an image, for minifying an image, for moving an image to a particular position on the retina, for changing a visual field, for increasing peripheral vision, for improving central vision, for altering an intensity of light entering the eye, for altering at least one spectrum of wavelength of light entering the eye, for treatment of a disorder of central vision, for treatment of age-related macular degeneration, for treatment of a disorder of peripheral vision, for treatment of a tapetoretinal degeneration, and for treatment of a cataract.

28. An intraocular implant for implantation into the interior of an eye, the eye having a pupil, an iris, and a retina, the retina having a macula, the implant comprising:
a. a body member, said body member having an anterior surface and a posterior surface, said body member having optical properties; and
b. at least two mirrors including at least one central mirror and at least one peripheral mirror, said at least one central mirror and said at least one peripheral mirror being contained within said body member, said at least one peripheral mirror being at least partially hidden behind the iris of the eye.

29. The implant of claim 28, wherein said implant is adapted for a position of fixation into the eye, said position of fixation being selected from the group consisting of anterior chamber fixation, posterior chamber fixation, capsular bag fixation, scleral fixation, intra-vitreous fixation, sulcus fixation, and iris supported fixation.

30. The implant of claim 28, wherein said anterior surface is of convex configuration and wherein said posterior surface is one of a convex configuration and a planar configuration.

31. The implant of claim 28, wherein said body member is foldable.

32. The implant of claim 28, wherein said implant further includes at least one loop for fixation in the eye.

33. The implant of claim 28, wherein said mirrors are configured so as to reflect a viewed image onto a preferred position of the retina of the eye.

34. The implant of claim 28, wherein said mirrors are adapted for at least one of multi-focal focusing and correction of higher order optical aberrations.

35. The implant of claim 28, wherein said central mirror has a shape with at least one characteristic selected from the group consisting of convex, concave, rounded, pointed, aspheric, irregular, fixed shape, and adjustable shape and wherein said peripheral mirror has a shape with at least one characteristic selected from the group consisting of complete circumferential ring, partial circumferential ring, convex, concave, aspheric, circular, elliptical, fixed shape, and adjustable shape.

36. The implant of claim 28, wherein said central mirror has an aperture therethrough.

37. The implant of claim 28, further including at least one adjustment mechanism for adjusting at least one feature of one of said mirrors, said adjustment mechanism being selected from the group consisting of a micromechanical mechanism, an electromagnetic mechanism, a photoelectric mechanism, and a piezoelectric mechanism, said at least one feature being selected from the group consisting of mirror shape, mirror curvature, and position of said mirrors, said implant being adapted for the treatment of presbyopia by said adjustment of said feature of said mirrors, said at least one adjustment mechanism being operable from outside the eye by an adjustment control element selected from the group consisting of a laser, ultrasound, light, a frequency emitter, an electromagnetic force element, a temperature control element, and a pressure control element.

38. The implant of claim 28, further comprising at least one prism, said at least one prism being adapted for at least one function selected from the group of: so as to divert at least a portion of a viewed image to a preferred part of the retina of the eye, so as to produce a continuity on the retina of the eye of a reflected visual image with a transmitted unreflected image, said at least one prism being selected from the group consisting of a holographic lens and a fresnel.

39. The implant of claim 28, wherein at least one of said mirrors is coated with a reflectance altering material for altering at least one light reflectance property thereof said reflectance altering material being adapted for at least one function selected from the group consisting of: for altering transmission of light through the implant and for blocking at least one specified spectrum of wavelength of light transmission through the implant.

40. The implant of claim 28, further including at least one filter for adjusting the light transmission through at least part of the implant.

41. The implant of claim 28, further including at least one lens.

42. The implant of claim 28, further including a conformer, said conformer being adapted for implantation into a structure of the eye, said conformer and said body member being adapted such that said body member is capable of being inserted and fixed into said conformer, said conformer further including at least one optical component, said conformer having at least one optical property, said conformer further including at least one loop for fixation in the eye, said implant being adapted so that said body member may be changed within said conformer.

43. The implant of claim 42, wherein said conformer is non-foldable.

44. The implant of claim 42, wherein said conformer is foldable.

45. The implant of claim 28, wherein at least one of said at least two mirrors is constructed from a plurality of component parts.

46. The implant of claim 28, wherein said body member encloses an inner cavity, wherein said cavity being filled with a material with desired optical properties, said material being selected from the group consisting of a gas, air, a liquid, water, an oil and a material with a graded index of refraction.

47. The implant of claim 28, wherein at least one of said mirrors is adapted for at least one function selected from the group consisting of: transmission of a laser beam for medical purposes, inverting an image, magnifying an image, minifying an image, moving an image to a particular position on the retina, changing a visual field, increasing peripheral vision, improving central vision, altering an intensity of light entering the eye, altering at least one spectrum of wavelength of light entering the eye, for treatment of a disorder of central vision, treatment of age-related macular degeneration, treatment of a disorder of peripheral vision, treatment of a tapetoretinal degeneration, and treatment of a cataract.

48. An intraocular implant for implantation into the interior of an eye, the eye having a pupil, an iris; and a retina, the retina having a macula, the implant comprising:
 a. a body member having an anterior surface and a posterior surface, said body member having optical properties; and
 b. two mirrors including a central mirror and a peripheral mirror, said two mirrors being contained within said body member, said central mirror having an aperture therethrough.

* * * * *